(12) United States Patent
Barket, Jr. et al.

(10) Patent No.: US 7,841,244 B2
(45) Date of Patent: Nov. 30, 2010

(54) APPARATUS AND METHOD FOR MOBILE COLLECTION OF ATMOSPHERIC SAMPLE FOR CHEMICAL ANALYSIS

(75) Inventors: Dennis Barket, Jr., Lafayette, IN (US); Garth E. Patterson, Brookston, IN (US); Mark Gregory, Lafayette, IN (US)

(73) Assignee: Griffin Analytical Technologies, Inc., West Lafayette, IN (US)

( * ) Notice: Subject to any disclaimer, the term of this patent is extended or adjusted under 35 U.S.C. 154(b) by 554 days.

(21) Appl. No.: 11/792,389

(22) PCT Filed: Dec. 6, 2005

(86) PCT No.: PCT/US2005/043953

§ 371 (c)(1),
(2), (4) Date: Sep. 24, 2007

(87) PCT Pub. No.: WO2006/062906

PCT Pub. Date: Jun. 15, 2006

(65) Prior Publication Data

US 2008/0229805 A1    Sep. 25, 2008

Related U.S. Application Data

(60) Provisional application No. 60/633,725, filed on Dec. 7, 2004.

(51) Int. Cl.
*G01N 1/24* (2006.01)
*G01N 1/14* (2006.01)

(52) U.S. Cl. .................. 73/862.21; 73/863.23

(58) Field of Classification Search .............. 73/863.21, 73/863.23, 863.25

See application file for complete search history.

(56) References Cited

U.S. PATENT DOCUMENTS 4,091,674 A    5/1978    Amey (Continued)

FOREIGN PATENT DOCUMENTS

WO    WO-00/26405    5/2000

(Continued)

OTHER PUBLICATIONS

Camel et al.; "Trace Enrichment Methods for the Determination of Organic Pollutants in Ambient Air"; Journal of Chromatography A., vol. 710, No. 1, pp. 3-19, (1995).

(Continued)

*Primary Examiner*—Lisa M Caputo
*Assistant Examiner*—Punam Roy
(74) *Attorney, Agent, or Firm*—Finnegan, Henderson, Farabow, Garrett & Dunner, LLP

(57) ABSTRACT

The present invention discloses a portable sampler for collecting an atmospheric sample. In one implementation, the portable sampler includes a portable housing with an interior portion; a sample inlet communicating between an area outside the housing and the interior portion of the housing; a sample cartridge in fluid communication with the sample inlet and adapted to store the atmospheric sample, the sample cartridge being removably secured within the housing; a pump disposed within the housing and in fluid communication with the sample inlet, the pump being arranged to draw the atmospheric sample from the area outside the housing into the sample cartridge through the sample inlet; and a carrier gas inlet communicating between the area outside the housing and the sample cartridge, the carrier gas inlet being configured to couple with a carrier gas source for sweeping the atmospheric sample from the sample cartridge into an analyzer while the sample cartridge is secured within the housing.

37 Claims, 7 Drawing Sheets

U.S. PATENT DOCUMENTS

| | | | |
|---|---|---|---|
| 4,170,901 A | 10/1979 | Conkle et al. | |
| 4,584,887 A | 4/1986 | Galen | |
| 4,718,268 A | 1/1988 | Reid et al. | |
| 5,124,274 A | 6/1992 | Ohki et al. | |
| 5,138,889 A | 8/1992 | Conrad | |
| 5,142,143 A | 8/1992 | Fite et al. | |
| 5,333,511 A * | 8/1994 | Boyum et al. | 73/864.34 |
| 5,500,369 A | 3/1996 | Kiplinger | |
| 5,585,575 A | 12/1996 | Corrigan et al. | |
| 6,321,609 B1 | 11/2001 | Mengel et al. | |
| 6,327,918 B1 * | 12/2001 | Lawless | 73/863.21 |
| 6,446,514 B1 | 9/2002 | Danylewych-May et al. | |
| 6,477,906 B1 | 11/2002 | Peterson | |
| 2004/0224422 A1 | 11/2004 | Bonne et al. | |

FOREIGN PATENT DOCUMENTS

| | | |
|---|---|---|
| WO | WO-02/40964 A1 | 5/2002 |

OTHER PUBLICATIONS

First Office Action in Chinese Patent Application No. 200580047850.6 (National Phase Application Corresponding to PCT/US2005/043953), issued Oct. 30, 2009 (8 pages, plus 9-page translation).

* cited by examiner

APPARATUS AND METHOD FOR MOBILE COLLECTION OF ATMOSPHERIC SAMPLE FOR CHEMICAL ANALYSIS

CROSS-REFERENCE TO RELATED APPLICATION

This application claims the benefit of U.S. Provisional Application No. 60/633,725, filed Dec. 7, 2004, by Dennis Barket, Garth Patterson, and Mark Gregory and titled APPARATUS AND METHOD FOR MOBILE COLLECTION OF ATMOSPHERIC SAMPLE FOR CHEMICAL ANALYSIS, the disclosure of which is expressly incorporated herein by reference.

BACKGROUND OF THE INVENTION

1. Field of the Invention

The field of the invention includes hand-held or portable devices for collecting and storing atmospheric samples for subsequent chemical analysis.

2. Description of Related Art

U.S. Pat. No. 6,477,906 (Peterson) purports to disclose a sampling system for capturing samples of trace elements in ambient air, the system including a multi-port valve coupled to a plurality of sorbent tubes. The multi-port valve is constructed and operated in a predetermined sequence to created a flow path through the multi-port valve, thereby directing an air sample to one sorbent tube at a given time and over a given time interval.

U.S. Pat. No. 5,124,274 (Carroll et al.) purports to disclose a sample gun for collecting vapors emanating from compounds such as explosives, the vapors being collected on a surface coated with gas chromatograph material which traps explosive vapors while repelling nitric oxide. The trapped vapors are concentrated in one or more cold spot concentrators before a high speed chromatograph separates the vapors.

U.S. Pat. No. 5,500,369 (Kiplinger) purports to disclose a hand-held portable sampler that uses a vacuum to induce the flow of air into an air chamber and around a deflector plate. The deflector plate is mounted substantially transverse to the airflow pattern and configured to disrupt the airflow so as to cause airborne particulates to impact a nutrient material contained in culture containers.

U.S. Pat. No. 6,321,609 (Mengel et al.) purports to disclose a gas sampling system that includes a rotating carousel for holding sample tubes. Each sample tube is sealed at each end by a cap that has a needle-pierceable septum by which a gas sample is inserted, and contains a solid collector material to trap chemical and biological contaminants in a gas sample drawn through the sample tube. Individual sample tubes are moved into and out of a sampling location by incremental rotation of the carousel.

U.S. Pat. No. 5,142,143 (Fite et al.) purports to disclose a preconcentrator for analyzing trace constituents in gases wherein a sample gas is introduced to a confined sorbent. The sorbent is thereafter evacuated by a vacuum pump and a low-pressure carrier gas passes through the sorbent while it is desorbing, wherein the desorbed trace constituents are carried by the carrier gas to a detector that operates at low pressure, such as a mass spectrometer.

SUMMARY OF A FEW ASPECTS OF THE INVENTION

Apparatus consistent with one embodiment of the invention provide a portable sampler for collecting an atmospheric sample. The portable sampler includes a portable housing with an interior portion; a sample inlet communicating between an area outside the housing and the interior portion of the housing; a sample cartridge in fluid communication with the sample inlet and adapted to store the atmospheric sample, the sample cartridge being removably secured within the housing; a pump disposed within the housing and in fluid communication with the sample inlet, the pump being arranged to draw the atmospheric sample from the area outside the housing into the sample cartridge through the sample inlet; and a carrier gas inlet communicating between the area outside the housing and the sample cartridge, the carrier gas inlet being configured to couple with a carrier gas source for sweeping the atmospheric sample from the sample cartridge into an analyzer while the sample cartridge is secured within the housing.

Apparatus consistent with another embodiment of the invention provide a system for collecting and analyzing an atmospheric sample. The system includes a handheld sampler configured to collect the atmospheric sample. The handheld sampler includes a sample inlet, a pump in fluid communication with the sample inlet, a sample cartridge in fluid communication with the sample inlet and the pump, the sample cartridge being disposed therebetween, and a carrier gas inlet in fluid communication with the sample cartridge, the sample cartridge being disposed between the carrier gas inlet and the sample inlet. The system also includes a sample analyzer configured to couple with the handheld sampler to receive and analyze the atmospheric sample from the sample cartridge in the handheld sampler, the sample analyzer including: an analyte inlet configured to fluidly couple with the sample inlet, a carrier gas source to fluidly couple with the carrier gas inlet; and an analysis module in fluid communication with the analyte inlet.

Apparatus consistent with another embodiment of the invention provide a system for collecting and analyzing an atmospheric sample. The system includes a handheld sampler configured to collect the atmospheric sample, the handheld sampler including: a sample inlet, a pump in fluid communication with the sample inlet, a sample cartridge in fluid communication with the sample inlet and the pump, the sample cartridge being disposed therebetween, and a carrier gas inlet in fluid communication with the sample cartridge, the sample cartridge being disposed between the carrier gas inlet and the sample inlet. The system also includes a sample analyzer configured to couple with the handheld sampler to receive and analyze the atmospheric sample from the sample cartridge in the handheld sampler, the sample analyzer including: a wand configured to couple with the handheld sampler to receive the atmospheric sample from the sample cartridge in the handheld sampler, including an analyte inlet configured to fluidly couple with the sample inlet, and a carrier gas source to fluidly couple with the carrier gas inlet; and an interface in fluid communication with the analyte inlet. The sample analyzer also includes an analysis module in fluid communication with the interface.

Methods consistent with another embodiment of the invention provide a method for collecting and analyzing an atmospheric sample with a handheld sampler using an sample analyzer having an analyte inlet and a source of carrier gas, the handheld sampler including a removably securable sample cartridge with a sample inlet, a pump, and a carrier gas inlet, the atmospheric sample comprising a mixture of at least a matrix and an analyte. The method comprises locating the handheld sampler at a site to be tested; activating the pump to draw the atmospheric sample through the sample cartridge via the sample inlet; absorbing the analyte from the atmospheric sample within the sample cartridge, while the matrix passes through the sample cartridge; coupling the handheld sampler to the sample analyzer, the coupling step including fluidly coupling the sample inlet to the analyzer analyte inlet and fluidly coupling the carrier gas inlet to the carrier gas source; and sweeping the analyte from the sample cartridge into the analyte inlet via the sample inlet by flowing a carrier gas through the sample cartridge via the carrier gas inlet, the sample cartridge remaining secured in the sampler during the sweeping step.

Methods consistent with another embodiment of the invention provide a method for collecting an atmospheric sample with a handheld sampler, the handheld sampler including a plurality of removably securable sample cartridges, a sample inlet, and a pump, the atmospheric sample comprising a mixture of at least a matrix and an analyte. The method includes locating the handheld sampler at a site to be tested; fluidly connecting the sample inlet with each respective one of the plurality of sample cartridges; activating the pump to draw the atmospheric sample simultaneously through each respective one of the plurality of sample cartridges via the sample inlet; absorbing a portion of the analyte from the atmospheric sample within each respective one of the plurality of sample cartridges; and removing one of the plurality of sample cartridges after the absorbing step, for archival purposes.

Methods consistent with another embodiment of the invention provide a method for collecting an atmospheric sample with a handheld sampler, the handheld sampler including a sample cartridge, a sample inlet, a pump, a memory unit, and a global positioning device, the atmospheric sample comprising a mixture of at least a matrix and an analyte. The method includes locating the handheld sampler at a site to be tested; activating the pump to draw the atmospheric sample through the sample cartridge via the sample inlet; determining the location of the atmospheric sample with the global positioning device, the global positioning device generating a GPS output; and storing the GPS output in the memory unit of the handheld sampler.

Additional objects and advantages of the invention will be set forth in part in the description which follows, and in part will be obvious from the description, or may be learned by practice of the invention. The objects and advantages of the invention may be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to the present exemplary embodiments of the invention.

One embodiment of the invention entails a hand-held or otherwise portable sampler for collecting and storing atmospheric samples of gasses, vapors, particles, or liquids for subsequent analysis, such as, e.g., chemical analysis. This embodiment may comprise a housing that contains the components of the sampler, the dimensions of the housing and the weight of the components contained therein being such that the sampler may be carried by hand. Alternatively or additionally, the hand-held sampler may be constructed to be easily carried, for example, on a user's back, or over a user's shoulder.

Figure 1A:
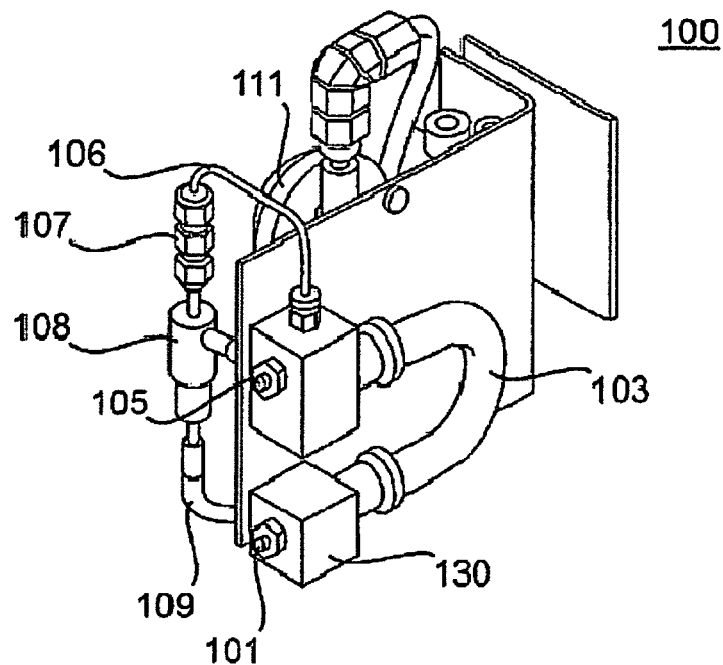
FIG. 1A shows a front perspective view of the components held within the apparatus housing of a handheld sampler in accordance with one embodiment of the invention.
Figure 1B:
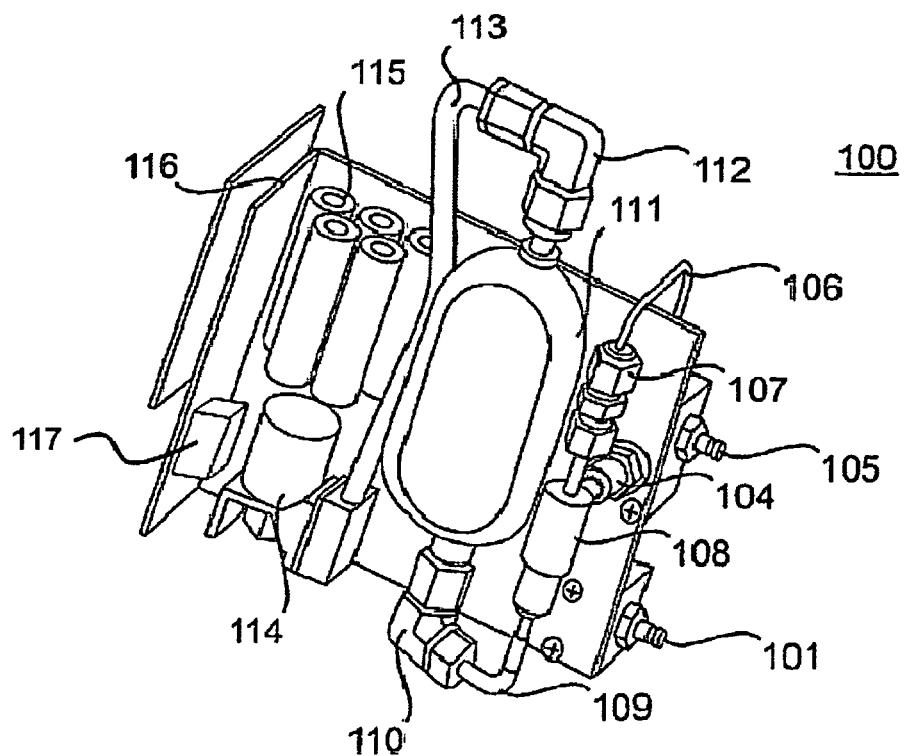
FIG. 1B shows a rear perspective view of the components held within the apparatus housing of a handheld sampler in accordance with one embodiment of the invention.
Figure 2A:
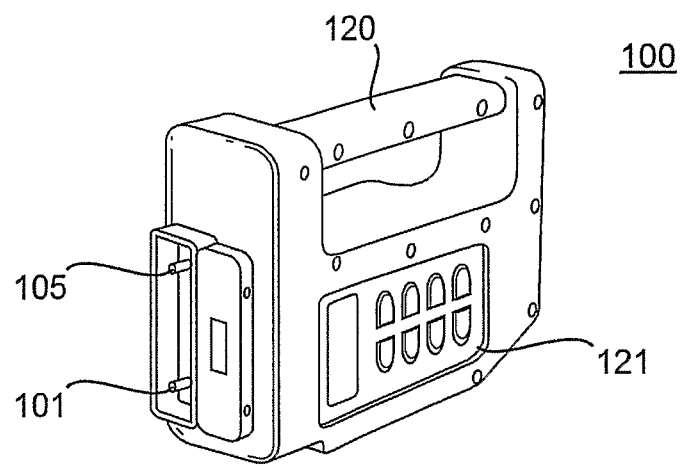
FIG. 2A shows a first perspective view of the apparatus housing of a handheld sampler in accordance with one embodiment of the invention.
Figure 2B:
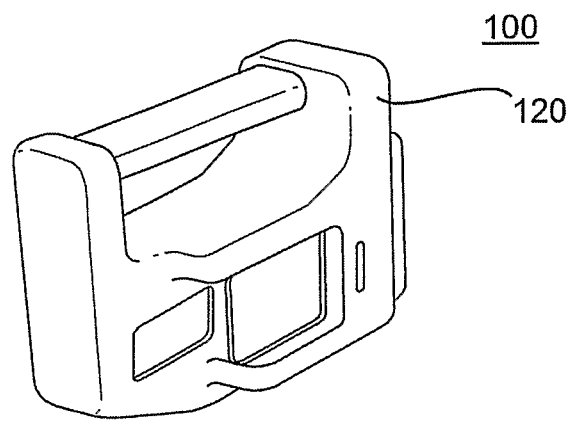
FIG. 2B shows a second perspective view of the apparatus housing of a handheld sampler in accordance with one embodiment of the invention.
Figure 2C:
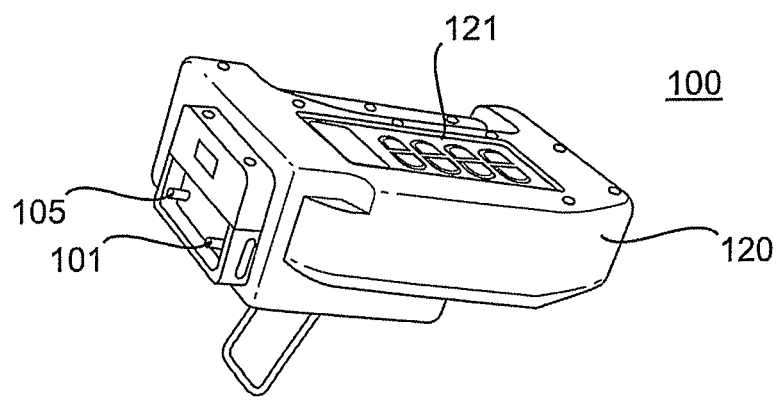
FIG. 2C shows a third perspective view of the apparatus housing of a handheld sampler in accordance with one embodiment of the invention.

FIGS. 1A-1B show two perspective views of the components held within the apparatus housing of a handheld sampler in accordance with one embodiment of the invention. FIGS. 2A-2C show three perspective views of the apparatus housing of a handheld sampler in accordance with one embodiment of the invention.

As shown in FIGS. 1A-1B, in this embodiment, a handheld sampler 100 includes a sample intake system, a sample cartridge 103, a power source 115, a sample output system, and a control unit 116. This embodiment is merely exemplary, and other embodiments may also be used.

As shown in FIG. 1A, in one embodiment, the sample intake system of handheld sampler 100 includes a sample inlet 101, a sample valve 108, a flowmeter 111, a sample pump 114, sample lines 106, 109, 113, and connectors 107, 110, and 112. In this embodiment, sample inlet 101 and sample pump 114 are connected by sample lines 106, 109, 113, and connectors 107, 110, and 112. Flowmeter 111, and sample valve 108 are disposed on the sample line therebetween. This embodiment is merely exemplary, and other embodiments may also be used.

In this embodiment, sample inlet 101 comprises an opening in communication with the atmosphere outside the housing. Sample inlet 101 may be a static opening that is always open, or alternatively, may include an inlet valve that is selectively opened when, for example, a sample is to be taken. The sample intake system is arranged in such a way that when sample pump 114 is activated and sample valve 108 is opened, the pump generates a negative pressure within sample line 106, 109, and 113 sufficient to flow a volume of gas from the atmosphere outside the housing and through sample inlet 101. Flowmeter 111 measures the amount of gas that has passed through the sample intake system. The individual components of the sample intake system are all well-known in the art. Furthermore, one skilled in the art would be able to easily conceive of alternate arrangements for achieving the objective of the sample inlet system, i.e., drawing a volume of gas through the apparatus.

The atmospheric samples collected by hand-held device 100 may include a matrix, such as, e.g., atmospheric gasses, including as oxygen and nitrogen, that contain materials to be analyzed, including potentially harmful chemical contaminants or pollutants, biological materials such as, e.g., anthrax spores, and radioisotopes to be subsequently analyzed. Hereinafter, the materials collected by hand-held sampler 100 for later analysis will be referred to as analytes. In yet another aspect of the invention, the sample intake system may be easily adapted to draw in volumes of matter in other than a gaseous state. The intake system may be adapted to draw in, for example, gasses bearing solid or liquid particulates, liquids, or colloidal suspensions.

As shown in FIGS. 1A-1B, in this embodiment, sample cartridge 103 is disposed along the sample line, in communication with sample inlet 101. Sample cartridge 103 is arranged to trap a sample of analytes borne by the volume of atmospheric gases as it passes through the sample intake system. The analytes trapped by sample cartridge 103 may be subsequently tested in a chemical analyzer, which may be, e.g., a mass spectrometer (MS) or a flame ionization detector (FID). Alternatively, the analytes trapped by sample cartridge 103 may be transferred to a chemical separation device, such as, e.g., a gas-chromatograph (GC). In a further embodiment, the trapped analytes may be transferred to a combination GC/MS, GC/electron capture detector (ECD), or GC/FID. In a first embodiment, sample cartridge 103 comprises one or more sorbent tubes. Alternatively, sample cartridge 103 may comprise disc filters, SPME fibers, evacuated cylinders, and/or any other trap that is known in the art. The present invention may further include an additional filter disposed at a point in the sample intake line upstream of sample cartridge 103 to filter debris and other solid or liquid particulates as desired. Such filters are also well-known in the art.

In one embodiment, it is desirable for a user to have access to sample cartridge 103. Generally, handheld sampler 100 includes a housing 120, such as that illustrated in FIGS. 2A-2C. Therefore, in this embodiment, the housing may include a hatch allowing access to the interior of the housing, generally, and sample cartridge 103, in particular. Sample cartridge 103 may be of a modular design that is easily integrated into the sample intake system. With such a construction, the present invention allows a user to easily interchange sample cartridges 103. A user may then select a type of sample cartridge 103 most appropriate for detection of an anticipated analyte.

In another embodiment (not shown), a pair of valves may be disposed on the sample intake line with sample cartridge 103 disposed therebetween. These valves may be opened to allow an atmospheric sample to flow through sample cartridge 103. The valves may subsequently be closed to isolate the sample within sample cartridge 103. This embodiment is merely exemplary, and other embodiments may also be used.

Figure 5:
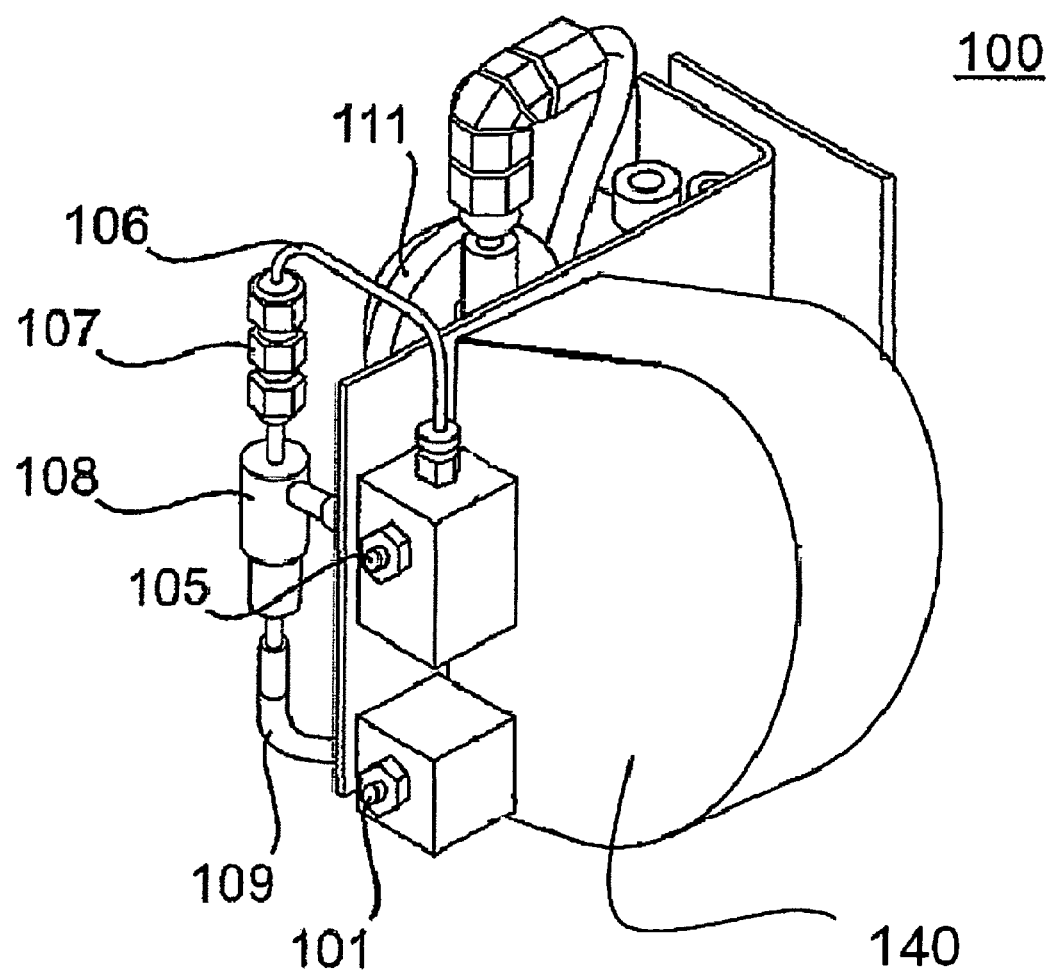
FIG. 5 shows a front perspective view of the components held within the apparatus housing of a handheld sampler, including a carousel, in accordance with one embodiment of the invention.

In yet another embodiment, a plurality of sample cartridges (not shown) may be carried on a carriage within the housing. The carriage may be arranged such that a first sample cartridge carried thereon is initially disposed at a first position on the sample intake line. Once a sample has been collected within the first sample cartridge, the carriage may then displace the first sample cartridge to a second position fluidly unconnected from the sample intake line. In so doing, the carriage may also displace a second sample cartridge carried thereon to the first position on the sample intake line for subsequently collecting a second sample. The carriage may comprise, for example, a rotational carousel 140 (shown in FIG. 5), the selective rotation of which may position each sample cartridge carried thereon in a first position on the storage intake line. Alternatively, the carriage may comprise a linear traversing carriage. Likewise, the linear translation of such a carriage sequentially positions each sample cartridge stored thereon in a first position on the storage intake line for sample collection. The incremental motion of the carriage may be powered by a stepper motor, for example. Alternatively, the carriage may be advanced between positions manually by a user. These embodiments are merely exemplary, and other embodiments may also be used.

Figure 6:
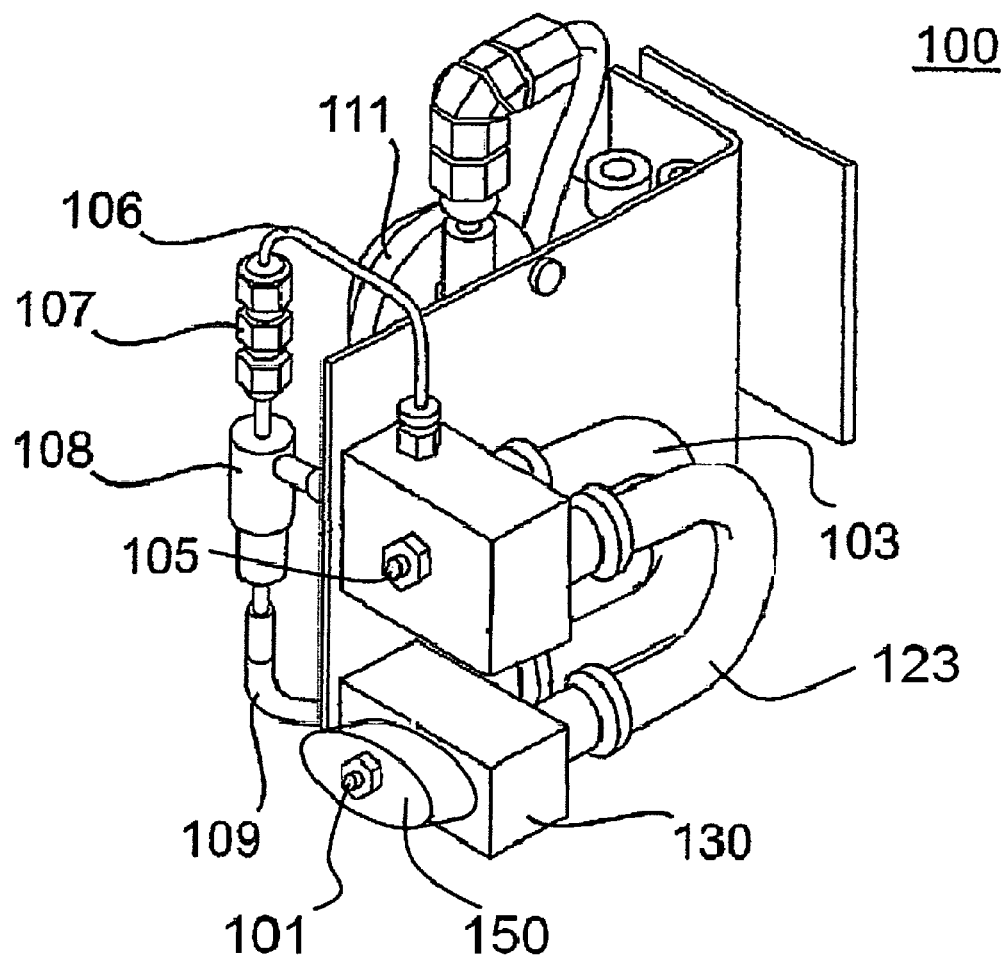
FIG. 6 shows a front perspective view of the components held within the apparatus housing of a handheld sampler, including a multi port valve, in accordance with one embodiment of the invention.

In another embodiment of the invention, a valve, or a combination of valves, may be configured to direct an atmospheric sample along a variable sample path through one of a plurality of sample cartridges (103 and 123, as shown in FIG. 6) as the atmospheric sample is drawn into the handheld sampler. For example, a valve, such as a multi-port valve 150 disposed downstream of the sample inlet, may be activated to direct a first atmospheric sample through a first sample cartridge 103. A second valve may cooperate with the first valve to fluidly connect the first sample cartridge with the pump to complete the sample path. To collect a second atmospheric sample in a second sample cartridge, the valves may be activated in order to direct the atmospheric sample through a second sample cartridge 123.

Figure 7:
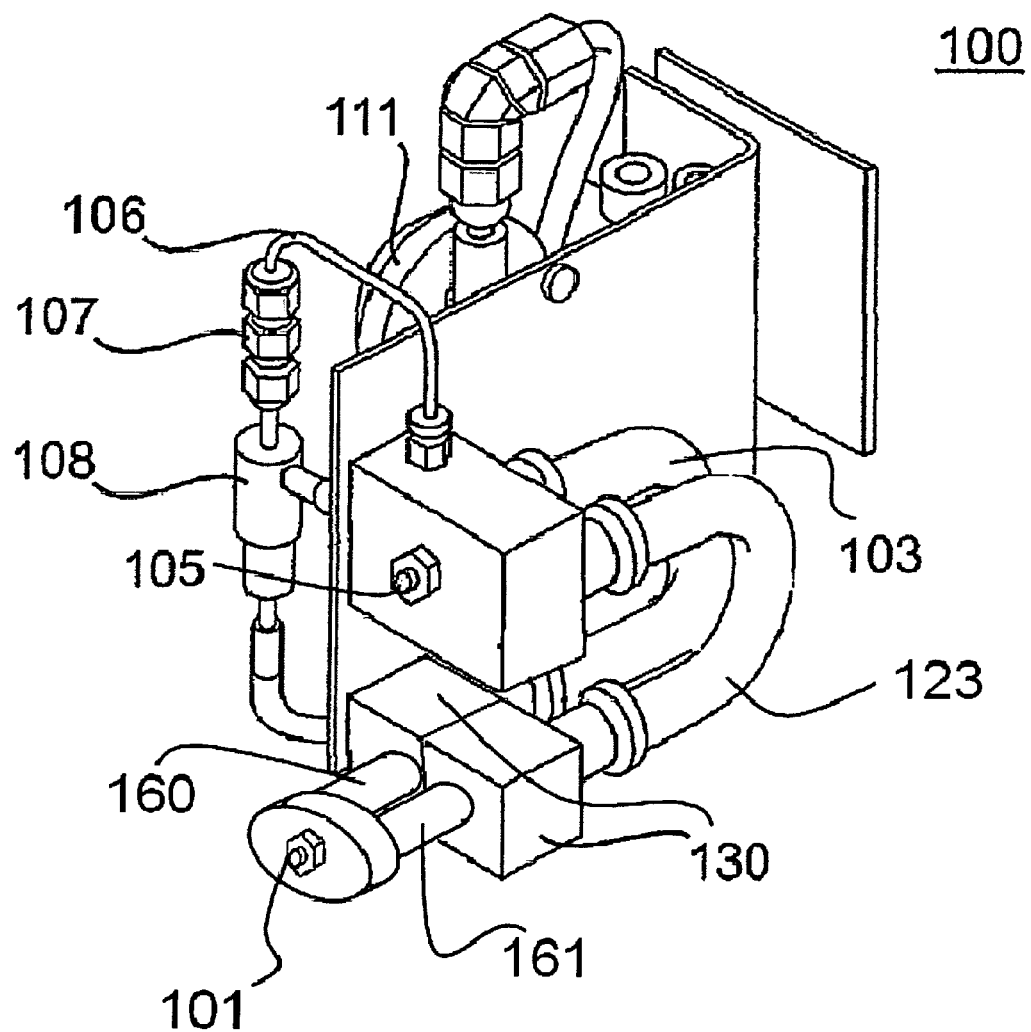
FIG. 7 shows a front perspective view of the components held within the apparatus housing of a handheld sampler, including a plurality of inlet paths, in accordance with one embodiment of the invention.

According to another embodiment of the invention, as shown in FIG. 7, the sample intake line may diverge into at least two sample lines (160 and 161) at point between the sample inlet and upstream of the sample cartridge. The sample lines may then converge into a single line downstream of the sample cartridge. A sample cartridge 103, 123 may then be inserted into each branch of the sample intake line. These parallel sample cartridges allow a user to collect and store multiple atmospheric samples from a single testing location. Once the sample is collected, at least one of the sample cartridges 103, 123 may be removed from the apparatus and stored for archival purposes or later analyzed to confirm and/or test the accuracy of the field analysis.

As shown in FIGS. 1A-2C, in one embodiment, handheld sampler 100 also includes control unit 116 for automatically controlling the operation of the apparatus. Control unit 116 may comprise a CPU (not shown), a memory unit (not shown), and a user interface 121. A user may interact with user interface 121 to select an operation mode stored in a portion of the memory unit. Once a particular operation mode is selected, the CPU runs the instructions stored in the memory unit that correspond to the selected operation mode. Different operation modes may be selected that operate the apparatus according to varying parameters. For example, an operation mode may be selected that operates the sample pump for a predetermined length of time. Another operation mode may be selected that operates the sample pump until a predetermined volume of gas has passed through the flowmeter. Various operation modes may be programmed into the memory by a user, as unique operation modes are developed. Alternatively, the apparatus may be operated manually.

In another embodiment of the invention, the memory unit may also store a sample identifier corresponding to a particular sample. This sample identifier may be entered manuallyby the user on the user interlace, or it may be sensed and stored automatically. For example, sample cartridge 103 may carry a coded identifier in the form of a microchip, barcode, or magnetic strip that acts as a unique identifier for that particular sample cartridge. Control unit 116 may include a reader to automatically read and store such a coded identifier. Likewise, hand-held sampler 100, itself, may be associated with an identifier that may be stored in the memory unit of the hand-held sampler. Control unit 116 may also comprise various sensors to measure certain parameters relating to a collected sample. These sensors may include, for example, pressure sensors and temperature sensors. These sensors may be configured to measure, e.g., the temperature or the pressure of the atmospheric sample, the temperature of the sorbent material, or the volume of gas that has flowed through the hand-held sampler. The output of these sensors may be sampled, either periodically or continuously, and stored in a portion of the memory unit corresponding to the sample identifier. The output of flowmeter 111 may also be sampled and stored in the memory unit. Alternatively or additionally, the volume of the atmospheric sample may be indirectly measured by collecting a sample at a given flow rate for a given length of time. The flow rate and the collection time may be used to determine the volume of the atmospheric sample, either manually or automatically be the control unit. The control unit may further include a GPS device 117 for precisely determining the location of a sample, which may also be stored in the memory unit. The date and time the sample is collected may also be stored in the memory unit. Alternatively, these and other data may be monitored by the user and entered into the memory unit manually via the user interface.

In another embodiment of the invention, as shown in FIGS. 1A-1B, hand-held sampler 100 may also include a sample output system for transferring the stored sample to the fieldable analyzer, which may be a fieldable chemical analyzer (e.g., a portable MS). The sample output system may include a carrier gas inlet 105 that intersects the sample intake line at a point such that sample cartridge 103 is disposed between carrier gas inlet 105 and sample inlet 101. Carrier gas inlet 105 may communicate with the atmosphere outside the housing. Carrier gas inlet 105 may be constructed to be coupled to a carrier gas source, such as a canister of pressurized Helium. The coupling may be any conventional coupling for gas lines well known in the art. The carrier gas source may be carried by, or integrated with, the analyzer. Alternatively, the carrier gas source may be stand alone or be carried by, or integrated with, hand-held sampler 100. Carrier gas inlet 103 may also include a normally-closed carrier gas inlet valve, which may be opened during transfer of the sample to the chemical analyzer. This embodiment is merely exemplary, and other embodiments may also be used.

Figure 3:
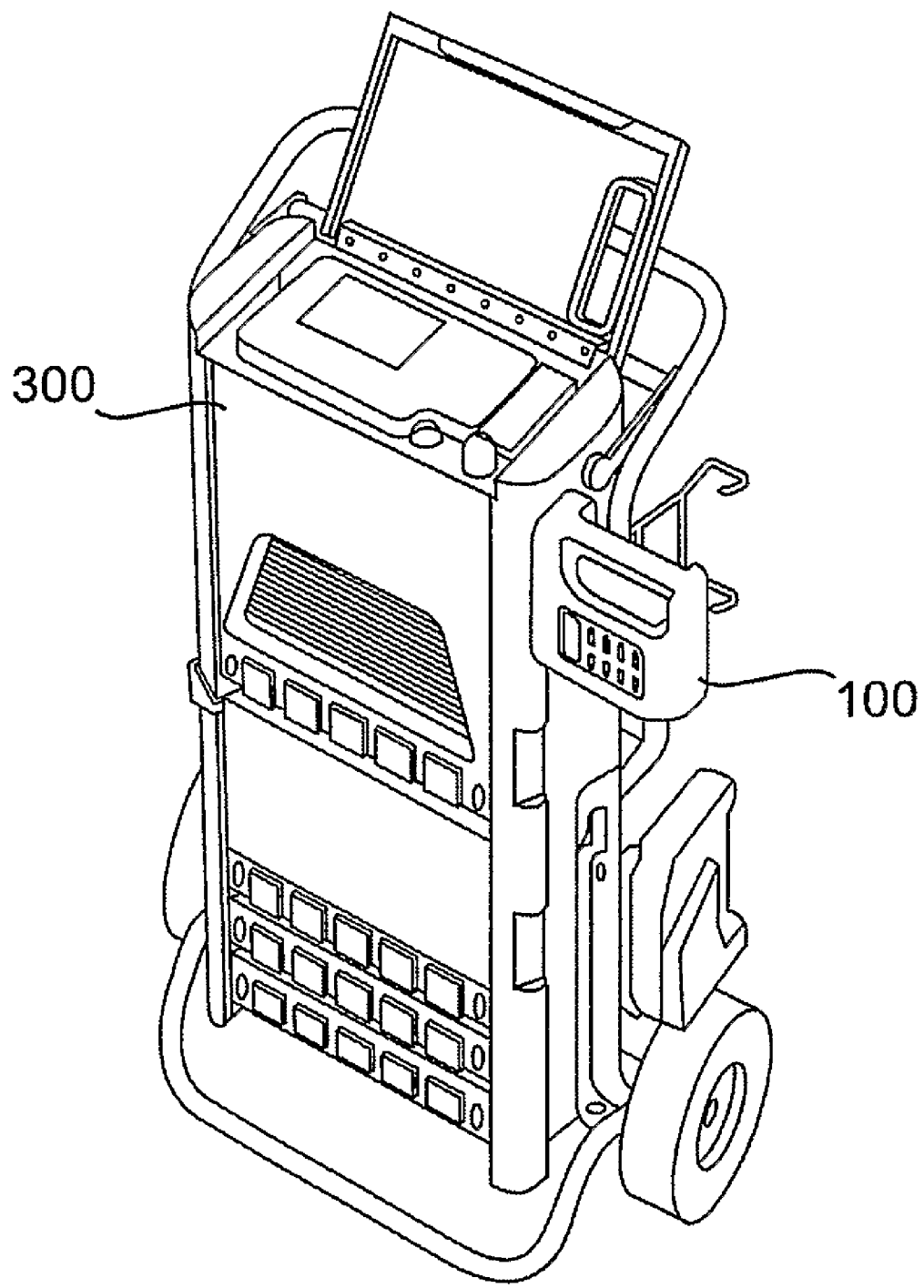
FIG. 3 shows a perspective view of a docking station for a handheld sampler in accordance with one embodiment of the invention.

In one embodiment, handheld sample 100 may be docked with a docking station in order to analyze the analytes. FIG. 3 shows a perspective view of a docking station for a handheld sampler in accordance with one embodiment of the invention. As shown in FIG. 3, in one embodiment, the sample inlet 101 may be constructed to couple with an inlet valve of an analyzer 300 in communication with the testing chamber of analyzer 300, which may be, e.g., a chemical analyzer. The coupling may be any conventional coupling for gas lines well known in the art. Alternatively, the coupling may be a relatively rigid, "male-female" coupling. When a user wishes to transfer the collected sample to chemical analyzer 300, handheld sampler 100 may be "docked" with chemical analyzer 300, whereby the sample inlet 101 may be coupled to the analyzer inlet valve and the carrier gas inlet 105 is coupled to a carrier gas source. By "docking," the analyzer may also support the hand-held sampler. This embodiment is merely exemplary, and other embodiments may also be used.

To transfer the collected sample to analyzer 300, control unit 116 may operate the valves within hand-held sampler 100 to define a purge path connecting the carrier gas source and chemical analyzer 300 via sample cartridge 103. The purge path may additionally be routed through flowmeter 111. For example, control unit 116 may close sample valve 108, thereby isolating sample pump 114 from the purge path, while opening the carrier gas inlet 105, sample inlet 101, and any valves that isolate the sample cartridge. Alternatively, the user may manually operate the valves.

Once the purge path is established, a pressure differential between the carrier gas source and the chemical analyzer test chamber forces the carrier gas through the purge path, and thus through the sample cartridge, and into the analyzer test chamber. The pressure differential may alternatively, or additionally, be achieved by a vacuum, or a sub-atmospheric pressure, within the test chamber. The flow of the carrier gas through the sample cartridge sweeps the analytes trapped therein from sample cartridge 103 and into the analyzer test chamber.

Control unit 116 may flow the carrier gas through the purge path according to an operation mode stored in the memory unit. For example, control unit 116 may open the valves establishing the purge path for a predetermined length of time, or alternatively, until a predetermined volume of carrier gas has flowed through the purge path. Alternatively, the user may manually control the operation of the purge path via the user interface.

In another embodiment (not shown), the docking station may be separate from the analyzer. In this embodiment, handheld sampler 100 can be docked with the docking station as discussed above. The docking station and handheld sampler 100 could then be docked with an analyzer to test the analytes. Alternatively, the docking station itself could remove the analyte from handled sampler 100 using the purge path method described above. Handheld sampler 100 could then be removed from the docking station for further use. The docking station would then be docked with an analyzer for analysis of the analytes.

Figure 4:
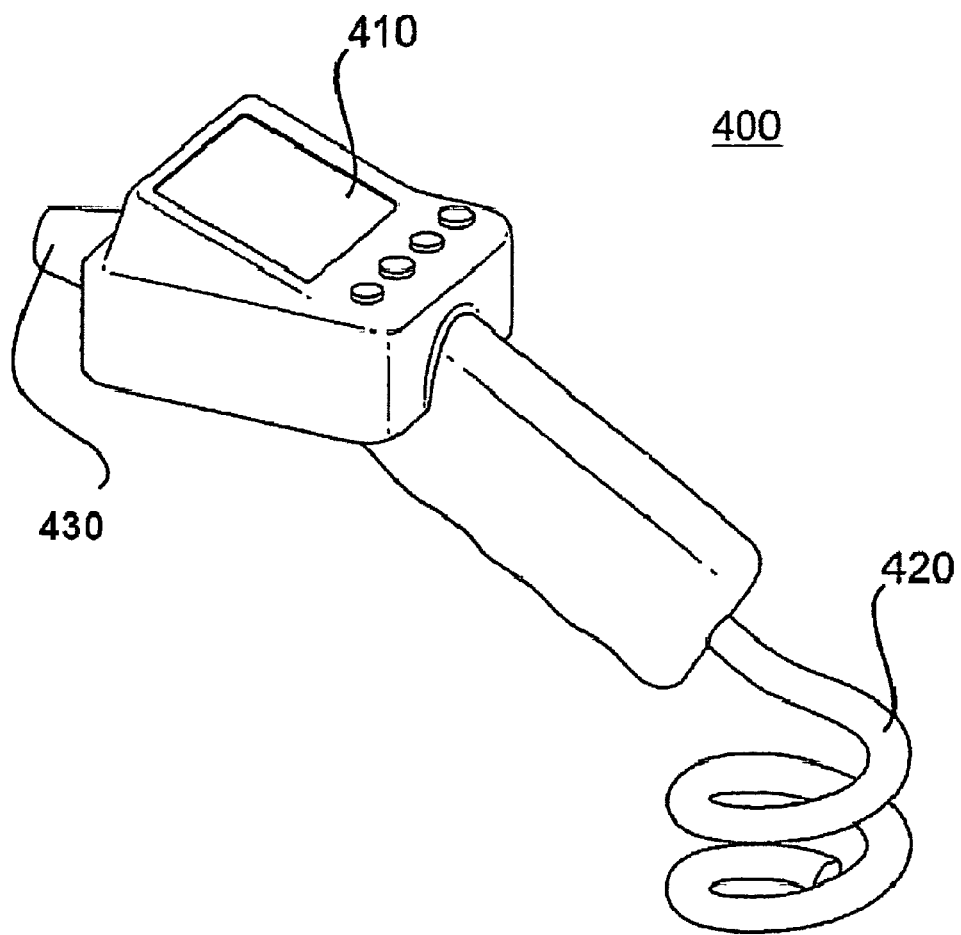
FIG. 4 shows a perspective view of a handheld wand in accordance with one embodiment of the invention.

In yet another embodiment, handheld sampler 100 may be docked with a handheld wand connected to an analyzer. FIG. 4 shows a perspective view of a handheld wand in accordance with one embodiment of the invention. In this embodiment, sample inlet 101 may be constructed to couple with an inlet valve 430 of handheld wand 400. The coupling may be any conventional coupling for gas lines well known in the art. Alternatively, the coupling may be a relatively rigid, "male-female" coupling. When a user wishes to transfer the collected sample to an analyzer, handheld sampler 100 may be "docked" with handheld wand 400. Using the methods described above, the analytes may then be transferred to handheld wand 400. As shown in FIG. 4, handheld wand 400 may also include a user interface 410 to operate handheld wand 400. In addition, handheld wand 400 also includes an interface 420 to connect with an analyzer. Interface 420 may include electrical connections and a sample path. The electrical connections would be used to operate handheld wand 400. The sample path would be used to transfer the analytes from handheld wand 400 to the analyzer. These embodiments are merely exemplary, and other embodiments may also be used.

As shown in FIG. 1A, in another embodiment of the invention, the sample output system may also include a heating block 130 for optionally applying heat to sample cartridge 103 prior to and/or during the transfer process. Heating block 130 may comprise any conventional heating apparatus for generating heat, such as a resistance-type heater. Applying heat to sample cartridge 103 volatilizes the analytes trapped therein. In such a condition, the analytes are more easily and efficiently removed from sample cartridge 103. In addition sample lines in handheld sample 100, analyzer 300 or handheld wand 400 may also be heated to more easily and efficiently transfer the analytes.

According to another aspect of the invention, control unit 116 may also include a communication link that couples with a control system of analyzer 300, the control system of chemical analyzer 300 further including a data storage unit. When hand-held sampler 100 is docked with chemical analyzer 300, the communication link may be coupled with the control system of chemical analyzer 300. The coupling may comprise any conventional device for passing digital data between electronic devices. The coupling may be a hard connection, such as a USB cable and port, for example. Alternatively, may be a wireless data transmission device. The communication link may be an "active" link, that is automatically activated by simply "docking" the devices together. Alternatively, the communication link may be manually activated by the user via the user interface. With control unit 116 coupled to the chemical analyzer control system, the control unit may download the data related to the collected sample from the memory unit to the data storage unit. The data may include one or more of, for example, a sample identifier, and information regarding the date and time of sampling, location data generated by the GPS unit, and physical measurements taken by the on-board sensors relating to temperature, pressure, and gas flow. Alternatively, or additionally, the control system may upload data to the control unit of handheld sampler 100. This data may include, for example, additional or updated operation modes.

As shown in FIG. 1B, in one embodiment of the invention, hand-held sampler 100 may also include a power source 115, such as a battery. More specifically, power source 115 may include rechargeable NiMH cells. Power source 115 supplies power to the components of hand-held sampler 100, including the control unit 114, pump 114, GPS unit, sensors, and valves. The sampler may also include a power link that, when the sampler is "docked" with the analyzer 300, couples the batteries with an external voltage source to re-charge the batteries.

A further aspect of the invention includes a method for collecting an atmospheric sample for subsequent analysis by an analyzer, such as a fieldable chemical analyzer 300, the method using an embodiment of the hand-held sampler apparatus described above. The method may involve transporting analyzer 300 to a test site. Fieldable chemical analyzer 300 may be, for example, a mass spectrometer (MS) dimensioned so as to be relatively portable, or fieldable. Alternatively, chemical analyzer 300 may be a gas chromatograph (GC/FID), or a combination GC/MS. As a further example, chemical analyzer 300 may be any chemical analyzer suitable for testing an atmospheric sample for chemical warfare agents, explosives, toxic industrial chemicals, or other pollutants, such as surface acoustic wave (SAW) and ion mobility spectrometer (IMS) systems. As a another example, analyzer 300 may be any kind of biological analyzer. Initially, hand-held sampler 100 may be docked to chemical analyzer 300. While docked, chemical analyzer 300 may upload information, such as operation modes, to control unit 116 of hand-held sampler 100 via the communication link. Once in the vicinity of the test site, hand-held sampler 100 may be un-docked from chemical analyzer 300.

A user may select an appropriate sample cartridge 103 according to the anticipated analytes, and insert sample cartridge 103 into the sample intake line. For example, if the site to be tested involves an industrial accident, such as a chemical spill, the user may select a specific sample cartridge particularly suited for trapping the chemicals that were likely involved. As a further example, if the site to be tested involves a possible terrorist attack, such as an airplane crash site, the user may select a specific sample cartridge particularly suited for trapping residual explosive chemicals. Control unit 116 may automatically detect and store a sample cartridge identifier after the storage device is installed in the sample intake line. Alternatively, the user may manually enter the identifier via the user interface.

The method of the present invention, may further involve transporting hand-held sampler 100 directly to a site to be tested. Once at the site, the user may select one of a plurality of operation modes stored in the control unit, thus activating hand-held sampler 100. Thus activated, control unit 116 may run the instructions contained in the selected operation mode. For example, control unit 116 may activate sample pump 114, open the sample valve 108 and the sample inlet 101, and close the carrier gas inlet 105. The action of pump 114 draws an atmospheric sample through the sample intake line. As the sample passes through sample cartridge 103, analytes are trapped while atmospheric gasses such as oxygen and nitrogen freely pass through sample cartridge 103. According to the parameters set by the selected operation mode, the sample may be taken, for example, for a predetermined length of time, or until a certain volume has passed through flowmeter 111. As the sample is being taken, control unit 116 may sample and record, in the memory unit, the output of various sensors, including temperature and/or pressure sensors. Further, control unit 116 may record, in the memory unit, the location of the sample generated by the GPS unit, as well as the date and time of the sample. Alternatively, the user may manually operate hand-held sampler 100.

Once the sample is collected and the related data is stored, the method of the present invention may further involve taking subsequent samples prior to returning to analyzer 300. If the hand-held sampler includes a carriage, a second sample cartridge may be advanced into the sample intake line either by control unit 116, or manually via user interface 121. With the second sample cartridge positioned in the sample intake line, the first sample cartridge is sealed to isolate the contents of the sample cartridge. With the second sample cartridge positioned in the sample intake line, the user may take a second sample substantially as discussed above. Further samples may likewise by collected according to the capacity of the sample cartridge carriage.

Once the desired number of samples have been collected, the method of the present invention may further include docking hand-held sampler 100 with analyzer 300, with a separate docking station or handheld wand 400. In so doing, the user may couple the sample inlet 101 to the analyzer inlet, and carrier gas inlet 105 to the carrier gas source. The user may also couple the communication link to the control system of analyzer 300, and the power link to the voltage source. Once hand-held sampler 100 is docked with the analyzer, control unit 116 may automatically initiate the process of transferring the stored sample to analyzer 300 according to an operation mode stored in the memory unit. Alternatively, the analyzer control system may initiate and control the transfer process. Alternatively, the user may initiate the process by selecting an operation mode via user interface 121. The transfer process involves opening a purge line through hand-held sampler 100 by opening the carrier gas inlet 105 and the sample inlet 101 and passing the pressurized carrier gas through the purge line, and thus through sample cartridge 103. As the carrier gas passes through sample cartridge 103, the carrier gas sweeps the analytes trapped within sample cartridge 103 into analyzer 300. Control unit runs the sample transfer process according to the selected operation mode. For example, the transfer process may run for a predetermine length of time, or until a predetermined volume of carrier gas is passed through the purge line. Alternatively, the user may opt to manually discontinue the transfer process.

Prior to and/or during the transfer process, the method of the present invention may also include activating heating blocks, such as heating block 130 integrated with the sampler. When the heating blocks are activated, the analytes trapped in the sample cartridge are volatilized, a condition whereby the analytes are more easily and efficiently removed from the sample cartridge.

If hand-held sampler 100 includes a carriage with multiple sample cartridges, the transfer process may run substantially as described above, except wherein the transfer process is temporarily halted as each sample cartridge is selectively positioned in the purge line.

While hand-held sampler 100 is docked with chemical analyzer 300, the method of the present invention may further involve downloading the data related to each collected sample from the memory unit of the hand-held sampler to the control system of the analyzer via the communication link. The download may occur automatically as the communication link is coupled to the chemical analyzer. Alternatively, the user may manually initiate the download via the user interface. The method of the present invention may also include coupling the power link of the hand-held sampler to the voltage source, thereby recharging the batteries that supply power to the hand-held sampler.

A further aspect of the present invention may relate to generating an analysis of an atmospheric sample in the field substantially according to the method and using the hand-held sampler with sample cartridges and analyzer described herein. The method may include providing a sample of analytes purged from an atmospheric sample to the analyzer 300. The analyzer may be, e.g., any fieldable chemical analyzer as herein described, including fieldable MS, GC, GC-MS, SAW, and IMS systems. Once the analytes are provided, the chemical analyzer analyzes the chemical components of the analytes and generates a corresponding output. This may be accomplished in the field, without the necessity of transporting the collected samples to a laboratory.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed:

1. A portable sampler for collecting an atmospheric sample, the portable sampler comprising:
 a portable housing with an interior portion;
 a sample inlet communicating between an area outside the housing and the interior portion of the housing;
 a sample cartridge in fluid communication with the sample inlet and adapted to store the atmospheric sample, the sample cartridge being removably secured within the housing;
 a pump disposed within the housing and in fluid communication with the sample inlet, the pump being arranged to draw the atmospheric sample from the area outside the housing into the sample cartridge through the sample inlet; and
 a carrier gas inlet communicating between the area outside the housing and the sample cartridge, the carrier gas inlet being configured to couple with a carrier gas source for sweeping the atmospheric sample from the sample cartridge into an analyzer while the sample cartridge is secured within the housing.

2. The sampler of claim 1 wherein the housing is configured to be handheld.

3. The sampler of claim 1, further comprising a control unit, wherein the control unit includes:
 a memory unit for storing an array of sample data;
 at least one sensor having an output, the at least one sensor configured to measure at least one of a temperature of the atmospheric sample, a volume of the atmospheric sample, a temperature of the sample cartridge, an elapsed time, and a pressure of the sample; and
 a central processing unit (CPU) configured to sample the output of the at least one sensor as the atmospheric sample is being collected, and to store the output in the memory unit as a part of the array of the sample data.

4. The sampler of claim 3, wherein the control unit further includes a global positioning device for determining a location of a sample site, the global positioning device generating a global positioning system (GPS) output, wherein the central processing unit (CPU) is further configured to sample the global positioning system (GPS) output as the atmospheric sample is being collected, and to store the global positioning system (GPS) output in the memory unit as a part of the array of sample data.

5. The sampler of claim 3, wherein the central processing unit (CPU) further includes a clock for generating a time stamp, wherein the central processing unit (CPU) is further configured to sample the time stamp as the atmospheric sample is being collected, and to store the time stamp in the memory unit as a part of the array of sample data.

6. The sampler of claim 3, further comprising a cartridge identifier for generating a sample identity, and wherein the central processing unit (CPU) is further configured to store the sample identity that is stored in the memory unit as a part of the array of sample data.

7. The sampler of claim 1, further comprising a power supply, wherein the power supply includes a rechargeable battery and an external power supply link configured to connect the rechargeable battery to a voltage source, whereby the rechargeable battery can be re-charged.

8. The sampler of claim 1, further comprising a carousel within the interior of the housing, the carousel adapted to carry a plurality of sample cartridges, the carousel being selectively moveable in order to sequentially advance a first sample cartridge from a first position in fluid communication with the sample inlet for taking a first atmospheric sample to a second position disconnected from the sample inlet for storing the first atmospheric sample.

9. The sampler of claim 1, further comprising:
 a plurality of sample cartridges; and
 a multi-port valve disposed between the sample inlet and the plurality of sample cartridges, the multi-port valve being configured to be incrementally engaged from a first position to fluidly connect the sample inlet to a first sample cartridge for taking a first atmospheric sample, to a second position to fluidly connect the sample inlet to a second sample cartridge for taking a second atmospheric sample.

10. The handheld sampler of claim 1, further comprising a heat source adapted to heat the atmospheric sample within the sample cartridge.

11. The handheld sampler of claim 1, wherein the sample inlet further comprises a plurality of sample inlet paths, each sample inlet path being in fluid communication with a respective one of a plurality of sample cartridges, the plurality of sample inlet paths arranged to divide the atmospheric sample among the plurality of sample cartridges.

12. The handheld sampler of claim 11, wherein a first sample cartridge stores a first part of the atmospheric sample for analysis by the analyzer, and a second sample cartridge stores a second part of the atmospheric sample for archival purposes.

13. The sampler of claim 1, wherein the sample cartridge comprises at least one of a sorbent tube, a disc filter, solid phase microextraction (SPME) fibers, and a polytetrafluoroethylene (PTFE) filter.

14. A system for collecting and analyzing an atmospheric sample, the system comprising:
 a handheld sampler configured to collect the atmospheric sample, the handheld sampler including:
  a sample inlet,
  a pump in fluid communication with the sample inlet,
  a sample cartridge in fluid communication with the sample inlet and the pump, the sample cartridge being disposed therebetween, and
  a carrier gas inlet in fluid communication with the sample cartridge, the sample cartridge being disposed between the carrier gas inlet and the sample inlet; and
 a sample analyzer configured to couple with the handheld sampler to receive and analyze the atmospheric sample from the sample cartridge in the handheld sampler, the sample analyzer including:
  an analyte inlet configured to fluidly couple with the sample inlet,
  a carrier gas source to fluidly couple with the carrier gas inlet; and
  an analysis module in fluid communication with the analyte inlet.

15. The system of claim 14, wherein the handheld sampler further includes:
 means including a sampler memory unit for collecting and storing an array of sample data related to the atmospheric sample, the array of sample data including at least one of a volume of the atmospheric sample, a temperature of the atmospheric sample, an elapsed time, and a pressure of the atmospheric sample; and
 wherein the system further comprises:
 communication means for transferring the array of sample data from the handheld sampler memory unit to an analyzer memory unit when the handheld sampler is coupled to the sample analyzer.

16. The system of claim 15, wherein the handheld sampler further includes:
 global positioning means for generating a global positioning system (GPS) output, the array of sample data further including the global positioning system (GPS) output.

17. The system of claim 14, wherein the handheld sampler further includes:
 sample identifier means for generating a sample identity, the array of sample date further including the cartridge identifier.

18. The system of claim 14, wherein the handheld sampler includes a rechargeable battery, and wherein the analyzer includes a power source, the system further including:
 means for electrically interconnecting the battery and the power source for charging the battery when the handheld sampler is coupled to the sample analyzer.

19. The system of claim 14, wherein the sample analyzer is configured to physically support the handheld sampler when the handheld sampler is coupled with the sample analyzer.

20. The system of claim 14, wherein the sample analyzer comprises one of a mass spectrometer, a flame ionization detector, a gas chromatograph-mass spectrometer, and a gas chromatograph-flame ionization detector.

21. The system of claim 14, wherein the sample analyzer comprises one of a surface acoustic wave system, and an ion mobility spectrometer system.

22. The system of claim 14, wherein the sample analyzer is a biological analyzer.

23. The system of claim 14, wherein the sample analyzer comprises a chemical analyzer for detecting a plurality of airborne chemicals in the atmospheric sample, the plurality of airborne chemicals including chemical warfare agents, explosives, toxic industrial chemicals, and pollutants.

24. The system of claim 14, wherein the sample analyzer is fieldable.

25. A system for collecting and analyzing an atmospheric sample, the system comprising:
 a handheld sampler configured to collect the atmospheric sample, the handheld sampler including:
  a sample inlet,
  a pump in fluid communication with the sample inlet,
  a sample cartridge in fluid communication with the sample inlet and the pump, the sample cartridge being disposed therebetween, and
  a carrier gas inlet in fluid communication with the sample cartridge, the sample cartridge being disposed between the carrier gas inlet and the sample inlet; and
 a sample analyzer configured to couple with the handheld sampler to receive and analyze the atmospheric sample from the sample cartridge in the handheld sampler, the sample analyzer including:
  a wand configured to couple with the handheld sampler to receive the atmospheric sample from the sample cartridge in the handheld sampler, including
   an analyte inlet configured to fluidly couple with the sample inlet, and
   a carrier gas source to fluidly couple with the carrier gas inlet; and
   an interface in fluid communication with the analyte inlet; and
  an analysis module in fluid communication with the interface.

26. A method for collecting and analyzing an atmospheric sample with a handheld sampler using an sample analyzer having an analyte inlet and a source of carrier gas, the handheld sampler including a removably securable sample cartridge with a sample inlet, a pump, and a carrier gas inlet, the atmospheric sample comprising a mixture of at least a matrix and an analyte, the method comprising:
 locating the handheld sampler at a site to be tested;
 activating the pump to draw the atmospheric sample through the sample cartridge via the sample inlet;
 absorbing the analyte from the atmospheric sample within the sample cartridge, while the matrix passes through the sample cartridge;
 coupling the handheld sampler to the sample analyzer, the coupling step including fluidly coupling the sample inlet to the analyzer analyte inlet and fluidly coupling the carrier gas inlet to the carrier gas source; and
 sweeping the analyte from the sample cartridge into the analyte inlet via the sample inlet by flowing a carrier gas through the sample cartridge via the carrier gas inlet, the sample cartridge remaining secured in the sampler during the sweeping step.

27. The method of claim 26, further comprising:
providing a first control unit on the handheld sampler, the first control unit comprising a memory unit for storing an array of sample data, and a central processing unit (CPU);
providing at least one sensor generating an output, the at least one sensor configured to measure at least one of: a temperature of the atmospheric sample, a temperature of the sample cartridge, a volume of the atmospheric sample, a pressure of the atmospheric sample, and an elapsed time;
sampling the output of the at least one sensor with the central processing unit (CPU);
storing the output in the memory unit as part of the array of sample data;
wherein the coupling step further includes providing a communication link between the first control on the handheld sampler and a second control unit on the sample analyzer; and
transmitting the array of sample data to the sample analyzer via the communication link.

28. The method of claim 27, further comprising:
providing a global positioning device on the handheld sampler;
determining a location of a sample site with the global positioning device, the global positioning device generating a global positioning system (GPS) output;
sampling the global positioning system (GPS) output with the central processing unit (CPU); and
storing the global positioning system (GPS) output in the memory unit as a part of the array of sample data.

29. The method of claim 27, further comprising:
providing a clock for generating a time stamp;
sampling the time stamp with the central processing unit (CPU); and
storing the time stamp in the memory unit as a part of the array of sample data.

30. The method of claim 27, the sample cartridge including a cartridge identifier, the method further comprising:
storing the cartridge identifier in the memory unit as a part of the array of sample data.

31. The method of claim 26, further comprising:
providing a rechargeable battery in the handheld sampler for supplying power to the handheld sampler;
providing an external voltage source apart from the handheld sampler;
providing a power supply link connected to the rechargeable battery; and
connecting the rechargeable battery to the external voltage source via the power supply link when the sampler is coupled to the sample analyzer, whereby the rechargeable battery is re-charged.

32. The method of claim 26, further comprising:
providing a multi-port valve disposed in the handheld sampler between the sample inlet and a plurality of sample cartridges; and
wherein the sweeping step includes incrementally actuating the multi-port valve to fluidly connect the sample inlet to a respective one of the plurality of sample cartridges.

33. The method of claim 26, further comprising:
providing a heat source in the handheld sampler; and
wherein the sweeping step includes applying heat to the analyte within the sample cartridge.

34. The method of claim 26, wherein the sample inlet further comprises a plurality of sample inlet paths, and the handheld sampler includes a plurality of sample cartridges, each of the plurality of sample cartridges being in fluid communication with a respective one of the plurality of sample inlet paths; and
wherein the method further comprises removing a sample cartridge after collecting an atmospheric sample but before the sweeping step, for archival purposes.

35. A method for collecting an atmospheric sample with a handheld sampler, the handheld sampler including a plurality of removably securable sample cartridges, a sample inlet, and a pump, the atmospheric sample comprising a mixture of at least a matrix and an analyte, the method comprising:
locating the handheld sampler at a site to be tested;
fluidly connecting the sample inlet with each respective one of the plurality of sample cartridges;
activating the pump to draw the atmospheric sample simultaneously through each respective one of the plurality of sample cartridges via the sample inlet;
absorbing a portion of the analyte from the atmospheric sample within each respective one of the plurality of sample cartridges;
removing one of the plurality of sample cartridges after the absorbing step, for archival purposes; and
sweeping the analyte from at least one of the plurality of sample cartridges into an analyzer while the at least one sample cartridge is secured within the handheld sampler.

36. A method for collecting an atmospheric sample with a handheld sampler, the handheld sampler including a sample cartridge, a sample inlet, a pump, a memory unit, and a global positioning device, the atmospheric sample comprising a mixture of at least a matrix and an analyte, the method comprising:
locating the handheld sampler at a site to be tested;
activating the pump to draw the atmospheric sample through the sample cartridge via the sample inlet;
determining the location of the atmospheric sample with the global positioning device, the global positioning device generating a global positioning system (GPS) output;
storing the global positioning system (GPS) output in the memory unit of the handheld sampler; and
sweeping the atmospheric sample out of the sample cartridge for analysis while the sample cartridge is secured within the handheld sampler.

37. A system for collecting and analyzing an atmospheric sample, the system comprising:
a handheld sampler configured to collect the atmospheric sample, the handheld sampler including:
a sample inlet,
a pump in fluid communication with the sample inlet,
a sample cartridge in fluid communication with the sample inlet and the pump, the sample cartridge being disposed therebetween, and a carrier gas inlet in fluid communication with the sample cartridge, the sample cartridge being disposed between the carrier gas inlet and the sample inlet; and a docking station configured to couple with the handheld sampler to receive the atmospheric sample from the sample cartridge in the handheld sampler, the docking station including:

an analyte inlet configured to fluidly couple with the sample inlet, and a carrier gas source to fluidly couple with the carrier gas inlet; and the docking station being configured to separately couple with a sample analyzer to send the atmospheric sample to the sample analyzer, the sample analyzer being physically separate from the docking station and including:

an analyte inlet configured to fluidly couple with the docking station, and an analysis module in fluid communication with the analyte inlet.

* * * * *

UNITED STATES PATENT AND TRADEMARK OFFICE
CERTIFICATE OF CORRECTION

PATENT NO. : 7,841,244 B2  
APPLICATION NO. : 11/792389  
DATED : November 30, 2010  
INVENTOR(S) : Dennis Barket, Jr. et al.

Page 1 of 1

It is certified that error appears in the above-identified patent and that said Letters Patent is hereby corrected as shown below:

In claim 17, column 13, line 60, "sample date" should read --sample data--.

In claim 26, column 14, line 49, "an sample analyzer" should read --a sample analyzer--.

Signed and Sealed this

Twenty-second Day of March, 2011

David J. Kappos
*Director of the United States Patent and Trademark Office*